United States Patent [19]

Kyle et al.

[11] Patent Number: 5,034,013

[45] Date of Patent: Jul. 23, 1991

[54] INTRAMEDULLARY NAIL

[75] Inventors: Richard F. Kyle, Minneapolis, Minn.; Robert A. Winquist, Seattle, Wash.; George E. Simpson, Ft. Wayne, Ind.; John D. Miser, Warsaw, Ind.; Mark A. Bryant, Auburn, Ind.

[73] Assignee: Zimmer Inc., Warsaw, Ind.

[21] Appl. No.: 577,041

[22] Filed: Aug. 31, 1990

Related U.S. Application Data

[63] Continuation of Ser. No. 342,032, Apr. 24, 1989, abandoned.

[51] Int. Cl.$^5$ .............................................. A61F 5/04
[52] U.S. Cl. .......................................... 606/62; 606/63
[58] Field of Search ....................... 606/59, 60, 61, 62, 606/63, 65, 66, 67, 68, 72, 73

[56] References Cited

U.S. PATENT DOCUMENTS

| | | | |
|---|---|---|---|
| D. 261,935 | 11/1981 | Halloran | D24/33 |
| D. 279,502 | 7/1985 | Halloran | D24/33 |
| D. 279,503 | 7/1985 | Halloran | D24/33 |
| D. 282,488 | 2/1986 | Kalen | D24/33 |
| 4,103,683 | 8/1978 | Neufeld | 128/92 YK |
| 4,446,857 | 5/1984 | Otte et al. | 128/92 YK |
| 4,475,545 | 10/1984 | Ender | 128/92 R |
| 4,519,100 | 5/1985 | Wills et al. | 623/16 |
| 4,522,202 | 6/1985 | Otte et al. | 128/92 R |
| 4,541,424 | 9/1985 | Grosse et al. | 128/92 VD |
| 4,621,628 | 11/1986 | Brudermann | 128/92 YD |
| 4,622,959 | 11/1986 | Marcus | 128/92 YK |
| 4,667,664 | 5/1987 | Taylor et al. | 128/92 VZ |
| 4,697,585 | 10/1987 | Williams | 128/92 YZ |
| 4,705,027 | 11/1987 | Klaue | 128/92 YY |
| 4,875,474 | 10/1989 | Border | 606/63 |

FOREIGN PATENT DOCUMENTS

| | | |
|---|---|---|
| 0008758 | 3/1980 | European Pat. Off. . |
| 0118778 | 9/1984 | European Pat. Off. . |
| 99642 | 3/1987 | European Pat. Off. . |
| 0273872 | 7/1988 | European Pat. Off. . |
| 1593440 | 4/1978 | United Kingdom . |
| 1593440 | 7/1981 | United Kingdom . |
| 2114005 | 1/1983 | United Kingdom . |
| 2167963 | 6/1986 | United Kingdom . |

OTHER PUBLICATIONS

Kempf et al., "Closed Lock Intramedullary Nailing".
Taylor et al., "Russell-Taylor Nail System".
Grosse et al., "The Grosse & Kempf Intramedullary Nailing System".

Primary Examiner—Robert A. Hafer
Assistant Examiner—Michael Brown
Attorney, Agent, or Firm—Sherman and Shalloway

[57] ABSTRACT

An intramedullary nail is disclosed having a tubular elongated body that includes a proximal head portion, an intermediate portion and a distal end portion. The intermediate portion has a longitudinal slot along one side thereof, a groove coextensive with a portion of the slot, and three other grooves spaced about the circumference of the body. This construction provides more desirable flexibility and allows improved revascularization about the nail. The nail is formed of a rod material and the slot and grooves are machined therein to the desired depth and shape.

17 Claims, 5 Drawing Sheets

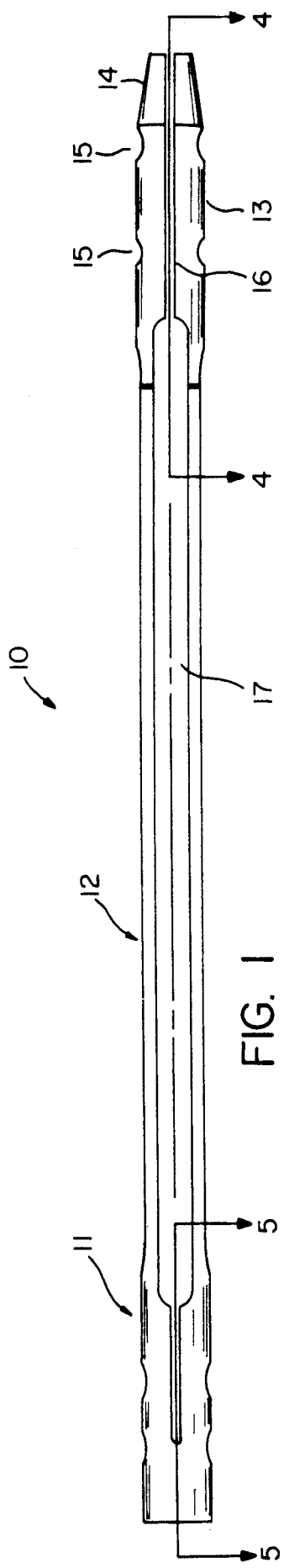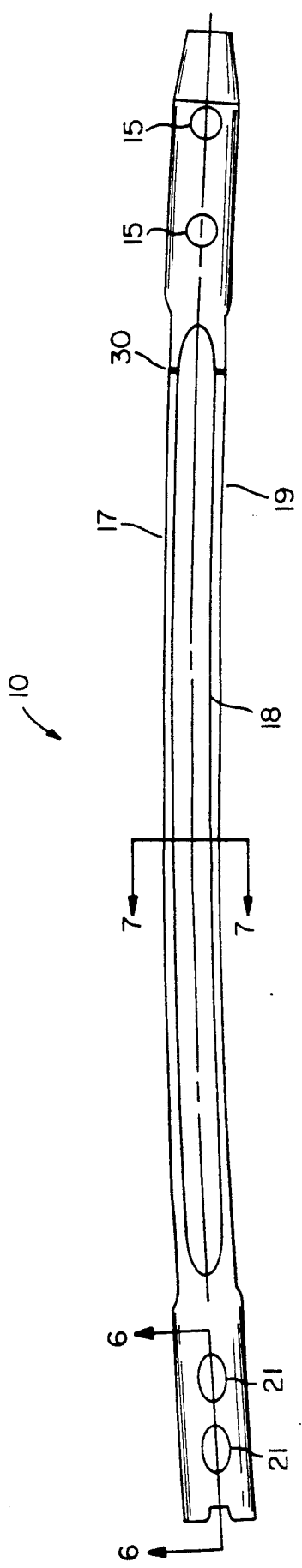

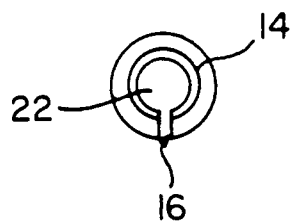
FIG. 8
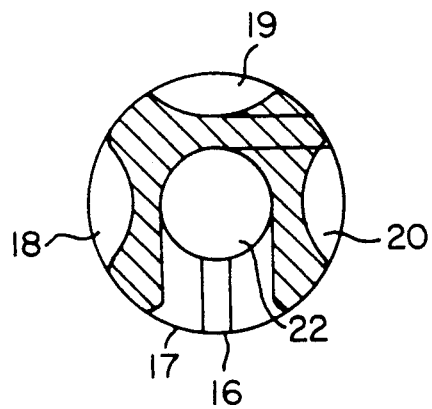
FIG. 14
FIG. 12
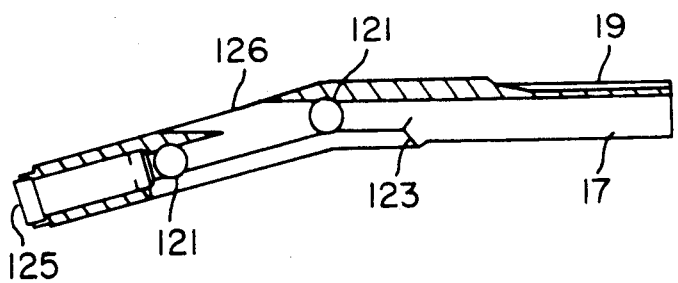
FIG. 13
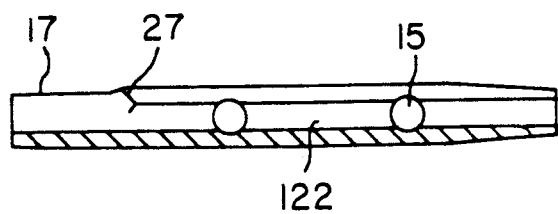

INTRAMEDULLARY NAIL

This application is a continuation, of application Ser. No. 07/342,032 filed Apr. 24, 1989 now abandoned.

BACKGROUND OF THE INVENTION

Field of the Invention

It has become accepted practice in the orthopedic field to use devices known as intramedullary nails to stabilize fractured bones. In particular, intramedullary nails are used for stabilizing fractures of the tibia and of the femur to thereby enable the bones to heal properly.

The nails are adapted for insertion into the intramedullary canal of the bone which may be reamed or left unreamed, depending on the situation at hand. Locking screws are often inserted through the bone to lock the nail in place. This method has proven valuable because it reduces the incidence and severity of malunion or displacement of the fracture. It allows the patient to apply weight to and walk on the injured bone earlier, thus, reducing the amount of muscle atrophy.

Various intramedullary nails have heretofore been known and disclosed int eh prior art. Prior art nails can be broken down by category:

First, many intramedullary nails have been proposed which are formed of a slid rod material. These have been found to be much too rigid to follow the usually imperfect intramedullary bone canal, and their insertion has all too often caused chipping of the bone material.

Nails formed of sheet metal have been proposed to provide greater flexibility. Some of these nails have been formed with closed cross-section and others have been formed into open cross-section configurations. To obtain desired flexibility/rigidity characteristics and to provide sufficient area about the nail to allow proper revascularization, such nails are generally formed with other than circular cross-section. This is, grooves on flat walls are often bent into the side walls of the sheet metal. Examples of such nails are found in U.S. Pat. No. 4,621,628 to Brudderman, U.S. Pat. No. 4,697,585 to Williams, European publication 0273872, U.S. publication 2,114,005, British publication 1,593,440, and Zimmer publication "A More Precise View of Interlocking Nails." Such sheet metal nails have proven to be relatively inefficient in their manufacture, and relatively difficult to modify in their configuration. More specifically, difficulties, inherent in the bending operation necessary to provide sheet metal nails with non-circular cross-section, have placed limitations on the ability to economically provide nails of cross-section which, for example, have grooves which are varied in their depth.

Other nails have been proposed which are formed from a rod material with a central longitudinal bore disposed therethrough. Such a bore provides a flexibility which is improved over that of the solid axls, but remains less than desirable. Examples of such nails are disclosed in U.S. Pat. No. 4,103,683 to Neufeld, U.S. Pat. No. 4,446,857 to Otte, et al., U.S. Pat. No. 4,622,959 to Marcus, European publication 0118778 and European publication 0008758.

Although the prior art nails have found varying degrees of success, there remains a need in the field for an intramedullary nail with a more desirable flexibility and with features which allow for easy and efficient modifications to the nail configuration during manufacture.

SUMMARY OF THE INVENTION

In accordance with the present invention there is provided a tubular intramedullary nail having an elongated body with a proximal head portion, an intermediate portion and a distal end portion. The nail is formed of a rod material with a centrally located longitudinal bore extending therethrough. A slot extends from the distal end longitudinally through a portion of the proximal head portion. Four longitudinal grooves are cut along a major portion of the intermediate portion and are equally spaced about the circumference of the nail; such groove cutting being known as fluting. One of the grooves is coextensive with a portion of the longitudinal slot.

This shape provides a more desirable flexibility because the grooves, in addition to the slot and the longitudinal bore, provide flexibility in various planes. Furthermore, the shape of the grooves allows them to be readily machined into the stock material with various shapes and depths. Thus, nails of various configuration can be easily manufactured without having to significantly modify the manufacturing operation. Rather, mere adjustment to, for example, the depth or radius of the groove cuts can provide the desired modifications. Furthermore, the lengths of the various grooves and slots cut into the nail can be readily varied. Variations in the lengths of grooves and slots is important in concentrating stresses to areas of the nail where it will not prove damaging and which are otherwise unstressed or less stressed.

The design of this nail further provides the availability of a greater area for revascularization in and around the nail. Because the nails can be readily provided with a variety of groove depths and shapes, the most advantageous configuration in terms of allowing revascularization can be formed for each nail.

Accordingly, it is an object of the present invention to provide intramedullary nails with improved flexibility.

It is also an object of the present invention to provide intramedullary nails formed such that their manufacturing operations can be readily adjusted to provide various nail configurations.

A further object of the present invention is to provide intramedullary nails which allow improved revascularization.

Yet another object of the present invention is to provide intramedullary nails wherein stresses are directed to areas of the nail which will not be damaged thereby.

A still further object of the present invention is to provide intramedullary nails with the above-noted advantages for use in the treatment of fractured femurs and for use in the treatment of fractured tibias and humerus.

Additional features, objects and advantages of the invention will become apparent from the drawings and the following detailed description.

BRIEF DESCRIPTION OF THE DRAWING FIGURES

The invention will be further described with reference to the accompanying drawings in which:

FIG. 1 is an anterior side plan view of an intramedullary nail according to the present invention for use in mending fractured femurs;

FIG. 2 is a side view of the femoral intramedullary nail shown in FIG. 1;

FIG. 8 is an end view of the distal end of the intramedullary nail shown in FIG. 1;

FIG. 12 is a cross-sectional view of an intramedullary nail taken along line XII—XII of FIG. 10;

FIG. 13 is a cross-sectional view of an intramedullary nail taken along line XIII—XIII of FIG. 10; and FIG. 14 is a cross-sectional view of an intramedullary nail taken along line XIV—XIV of FIG. 11.

DESCRIPTION OF THE PREFERRED EMBODIMENTS

Figure 3:
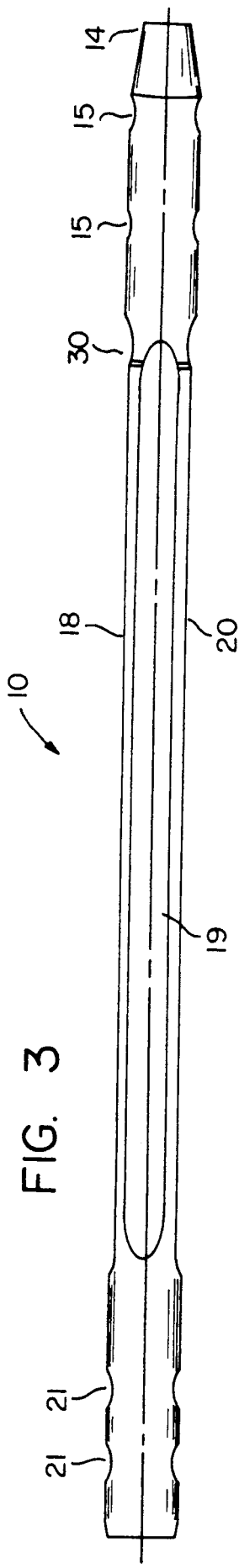
FIG. 3 is a posterior side plan view of the femoral intramedullary nail shown in FIG. 1.
Figure 10:
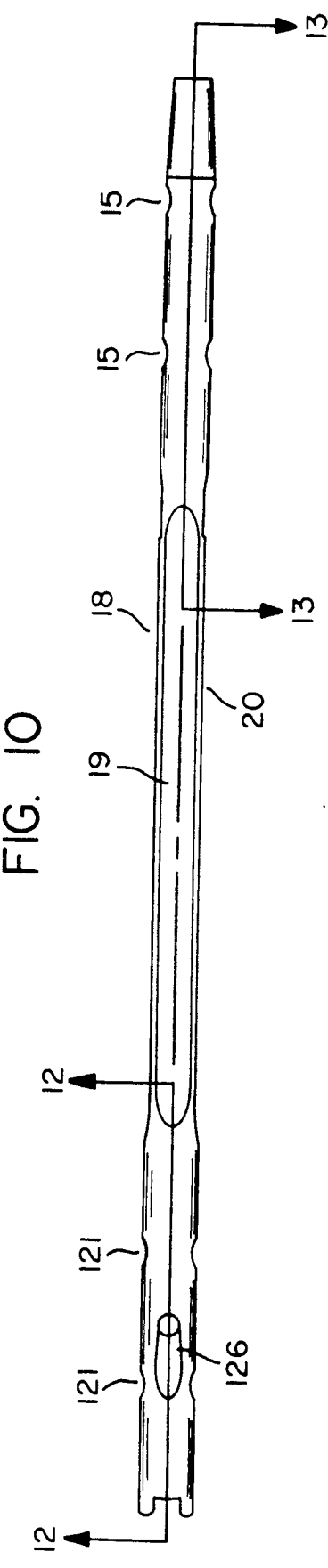
FIG. 10 is a posterior side plan view of the intramedullary nail shown in FIG. 9.
Figure 4:
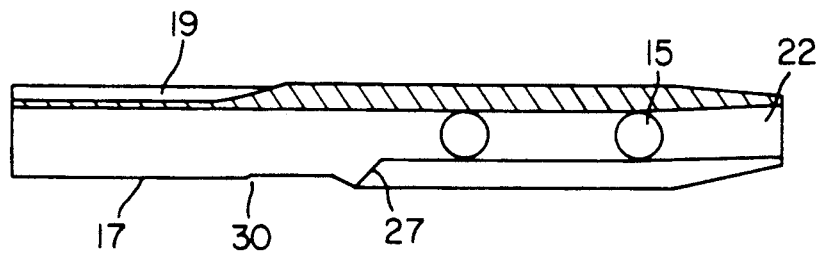
FIG. 4 is a cross-sectional view of an intramedullary nail taken along line IV—IV of FIG. 1.

FIG. 1 shows an improved intramedullary nail 10. The nail is formed of a solid rod material with a centrally located longitudinal bore therethrough to form a hollow elongated body with a proximal head portion 11, an intermediate portion 12 and a distal end portion 13. The distal end portion includes a tapered point 14.

This femoral nail 10 is insertable into the intramedullary canal of the femur and includes holes 15 at its distal end for reception of locking screws which hold the nail against movement both axially and torsionally. The proximal head portion also includes holes 21 for reception of locking screws.

The longitudinal bore 22 extends throughout the length of the nail. This bore not only provides added flexibility to the nail but also provides for the reception of a guide wire which aids in the insertion of the nail into the bone canal.

A slot 16, which radiates outwardly from the bore 22 to the nail surface, extends longitudinally along the anterior side of the nail from the point 14 up through a portion of the proximal head portion. This slot allows for greater flexibility of the nail and allows the distal portion of the nail to be squeezed together while first being inserted into the canal. Upon insertion, this portion of the nail expands and helps to hold the nail against movement within the canal. Note that the slot 16 extends upwardly to just above the apertures 21 (to be described later). This is important because the end of this slot is a point of stress concentration and the proximal end of the nail has a lesser amount of stress induced therein than other portions of the nail. The slot ends below the head of the nail, however, so as to provide an adequately strong insertion point for an insertion tool.

A longitudinal groove 17, which is coextensive with a portion of the slot 16, radiates outwardly from the bore 22 to the outer periphery of the nail body. The end 23 of groove 17 nearest to the lead of the nail is angled inwardly toward the proximal end of the nail so that the guide wire does not catch on a corner when the nail is inserted over the guide wire. Similarly, the end 27 of the groove 17 nearest to the point 14 of the nail is angled inwardly toward point 14 so that the guide wire does not catch on a corner in the event that a reinsertion of the guide wire into the bore 22 is required after its initial removal.

Along with groove 17, three other grooves 18, 19 and 20 extend along the intermediate portion 12 of the nail and are spaced about the periphery of the nail. Each end of each of the grooves is preferably gradually tapered outwardly. Although the grooves 17, 18, 19 and 20 can be formed of various depths and with various lengths, in the preferred embodiment the groove 17 on the anterior side of the nail is the longest of the four grooves, the groove 19 on the posterior side of the nail is the shortest of the four grooves and the two remaining grooves 18 and 20 are of a length intermediate that of grooves 17 and 19. This length distribution provides that the stresses incident in the nail will be directed around to the anterior side of the nail where they are more readily dissipated, especially due to the presence of the slot 16 on the anterior side of the nail. Furthermore, in the preferred embodiment, at least grooves 18 and 20 are of equal depth and shape.

An offset neck 30 is formed near the distal end portion 13 of the nail so as to provide a reduced distal diameter. This allows for easier insertion of the nail into the intramedullary canal, and if reaming of the canal is necessary, it prevents the requirement of over-reaming. Although the neck 30 can be formed at various angles, in the preferred embodiment, the neck is formed by a 30 degree angle radiating inwardly toward the distal end.

As previously mentioned, holes 15 and 21 are provided at each end of the nail and are adapted for the receipt of locking screws. In this femoral nail embodiment, the holes 15 are preferably transverse and the holes 21 are preferably mutually perpendicular and at angles of 45 degrees with respect to the longitudinal axis of the nail.

Figure 5:
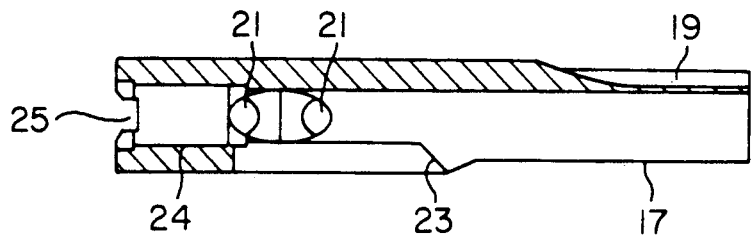
FIG. 5 is a sectional view of an intramedullary nail taken along line V—V of FIG. 1.
Figure 6:
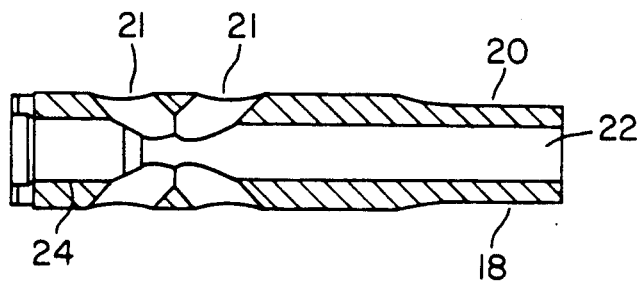
FIG. 6 is a cross-sectional view of an intramedullary nail taken along line VI—VI of FIG. 2.
Figure 7:
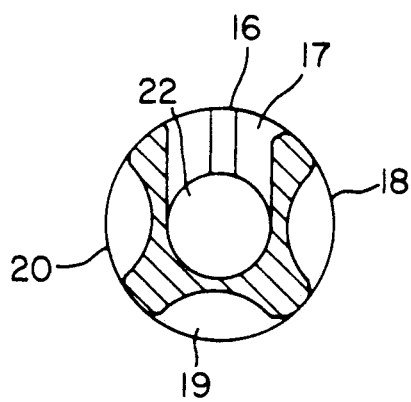
FIG. 7 is a cross-sectional view of an intramedullary nail taken along line VII—VII of FIG. 2.
Figure 9:
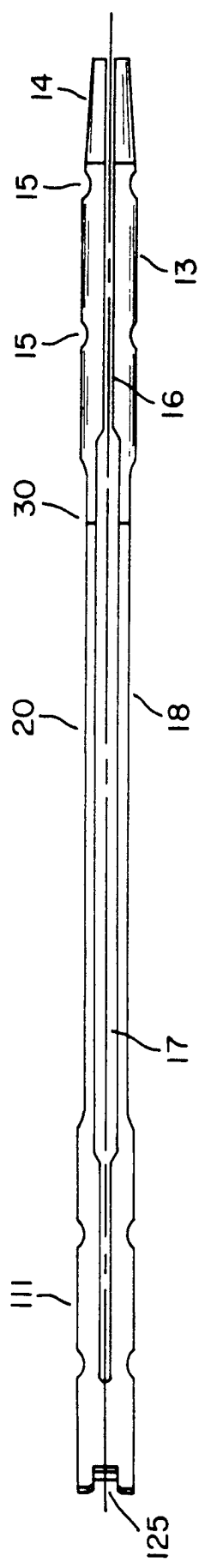
FIG. 9 is an anterior side plan view of an intramedullary nail according to a second embodiment of the present invention for use in mending fractures of the tibia or humerus.
Figure 11:
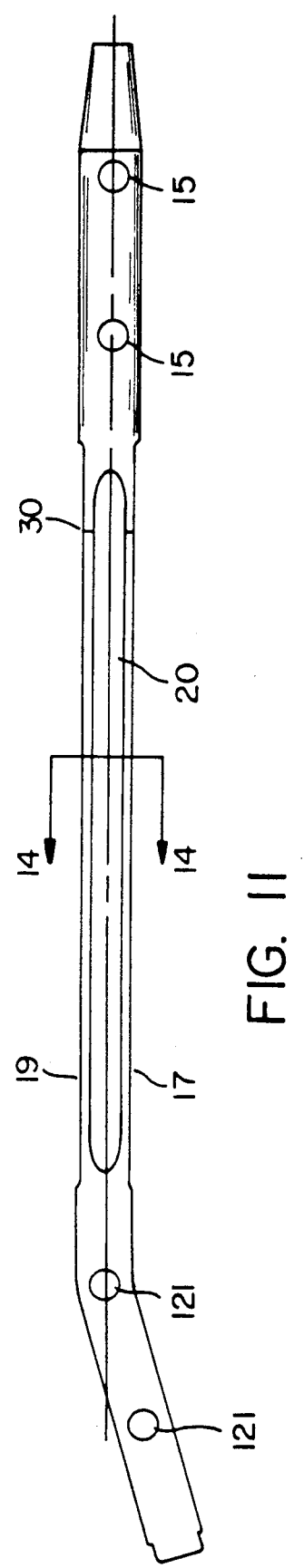
FIG. 11 is a side view of the tibial or humeral intramedullary nail shown in FIG. 9.

As shown in FIG. 5, the end of the head portion is provided with a screwthreaded bore 24 and a slot 25. These provide for insertion of tools used for inserting the nail into the canal, for angularly orienting the nail, and for aligning the locking screws into the holes 15 and 21.

Referring now to FIGS. 7 through 12, a second embodiment is shown in which like elements are designated by like numerals. So as to eliminate redundancy, features of this tibial nail embodiment which are the same as features of the femoral nail embodiment will not be described a second time. Thus, it will be understood that features of the second embodiment not specifically described are equivalent to corresponding features of the first embodiment.

In this embodiment, the hollow tibial intramedullary nail 100 has an elongated body with a distal end portion 13, an intermediate portion 12 and a proximal head portion 111 which is angled with respect to the intermediate portion. Tibial nail 100 is adapted for use in the tibia and, as with femoral nail 10, is adapted for insertion into the intramedullary canal.

The distal end portion 13 is identical to that of the femoral nail and includes a tapered point 14 and transverse locking screw holes 15. Also a slot 16 extends from the point 14 up through a portion of the proximal head portion 12.

As with the femoral nail, the tibial nail includes longitudinal grooves 17, 18, 19 and 20 spaced about the periphery of the intermediate portion 12, with groove 17 coextending with a portion of slot 16 and radiating outwardly from bore 22 to the outer periphery of the nail body. The grooves can be cut to various depths to provide various flexibility characteristics and to allow different amounts of area open to revascularization.

The end of the head portion 111 includes a screwthreaded bore 124 and a slot 125 for the receipt of tools used for insertion of the nail into the canal, for properly angularly orienting the nail into the canal, and for aligning the locking screws with the holes 15 and 121.

The tibial nail, unlike the femoral nail, has its head portion angled with respect to the intermediate portion, and includes transverse holes 121 rather than angled holes for receiving the locking screws. The tibial nail, like the femoral nail, includes a longitudinal bore 122 along the length of its axis. An opening 126 is provided at the outside of the bend in the head portion so that the longitudinal bore 122 remains straight. This is necessary because the guide wires used for insertion of the nail are generally too rigid to go around the bend in the head portion.

The intramedullary nails described above are preferably made of stainless steel but may be of any material commonly used for this type of device. Although the nails can be of any useful dimensions, the femoral nails preferably have a length from 300 millimeters to 500 millimeters and a diameter from 10 millimeters to 20 millimeters and the tibial and humeral nails preferably have a length from 240 millimeters to 380 millimeters and a diameter from 9 millimeters to 15 millimeters.

Many variations of the embodiments disclosed may be made without departing from the spirit and scope of the invention. It is to be understood, therefore, that this invention is not to be limited to the disclosed embodiments except as defined in the appended claims.

What is claimed is:

1. An intramedullary nail comprising
an elongated body having a proximal head portion with a proximal end, a distal end portion with a distal end and an intermediate portion interconnecting said proximal head portion and said distal end portion;
said elongated body having a centrally located longitudinal bore through the center thereof, said longitudinal bore having a predetermined diameter;
said proximal head portion having at least one proximal locking screw hole through said proximal head portion intersecting said longitudinal bore;
said elongated body having a longitudinally elongated slot along an anterior side thereof, said slot longitudinally extending from said distal end to beyond said at least one proximal locking screw hole, said slot radially extending from said bore outwardly to an outer periphery of said elongated body, said slot radially extending transverse to a plane defined by said at last one proximal locking screw hole and said longitudinal bore, said slot having a widened portion substantially longitudinally coextensive with said intermediate portion, said widened portion having a width substantially equal to said diameter of said longitudinal bore;
said intermediate portion having three longitudinally elongated grooves spaced about an outer periphery of said intermediate portion, a first one of said grooves being disposed on a posterior side of said intermediate portion diametrically opposite from said elongated slot, a second one of said three grooves being disposed 90 degrees circumferentially from said slot and said first groove, and a third one of said three grooves being disposed diametrically opposite from said second groove.

2. The intramedullary nail of claim 1, wherein said widened portion of said slot is longitudinally longer than said first, second and third grooves.

3. The intramedullary nail of claim 2, wherein said first groove is longitudinally shorter than said second and third grooves.

4. The intramedullary nail of claim 1, wherein said at least one proximal locking screw hole intersects said longitudinal bore non-transversely.

5. The intramedullary nail of claim 4, further comprising at least one distal locking screw hole through said distal end portion transversely intersecting said longitudinally bore, said at least one distal locking screw hole and said longitudinal bore defining a plane transverse to said radial extension of said slot.

6. The intramedullary nail of claim 5, wherein said elongated body is bent slightly along its longitudinal extent.

7. The intramedullary nail of claim 6, wherein said proximal head portion is substantially colinear with said intermediate portion.

8. The intramedullary nail of claim 1, wherein said slot terminates longitudinally intermediate said proximal locking screw hole and said proximal end.

9. The intramedullary nail of claim 1, wherein said at least one proximal locking screw hole intersect said longitudinal bore transversely.

10. The intramedullary nail of claim 9, further comprising at least one distal locking screw hole through said distal end portion transversely intersecting said longitudinal bore, said at least one distal locking screw hold and said longitudinal bore defining a plane transverse to said radial extension of said slot.

11. The intramedullary nail of claim 10, wherein said intermediate portion is collinear with said distal end portion.

12. The intramedullary nail of claim 11, wherein said head portion is angled obtusely with respect to said intermediate portion.

13. The intramedullary nail of claim 12, wherein said longitudinal bore remains linear through its length and exits through a hole in a side of said angled proximal head portion.

14. The intramedullary nail of claim 13, wherein said proximal head portion is provided with a screwthreaded end bore for engagement with a tool.

15. The intramedullary nail of claim 1, wherein each end of each of said three longitudinally extending grooves is tapered gradually toward the outer surface of said elongated body.

16. The intramedullary nail of claim 1, wherein said widened portion of said slot comprises a first end located nearest said proximal head portion and a second end located nearest said distal end portion, said first end including a first end wall which radiates outwardly and angles away from said proximal head portion, and said second end including a second end wall radiating outwardly and angled away from said distal end portion.

17. An intramedullary nail comprising a longitudinally elongated body having a proximal head portion, a distal end portion and an intermediate portion interconnecting said proximal head portion and said distal end portion; a centrally located longitudinal bore of predetermined diameter extending through said elongated body; a longitudinally elongated slot formed along an anterior side of said elongated body, said slot radially extending from said bore outwardly to an outer periphery of said elongated body and having a widened portion coextensive with said intermediate portion of a width substantially equal to said diameter of said longitudinal bore; at least two longitudinally elongated grooves spaced about an outer periphery of said intermediate portion.

* * * * *